(12) United States Patent
Saur (10) Patent No.: US 12,408,988 B2
(45) Date of Patent: Sep. 9, 2025

(54) METHOD AND SYSTEM FOR DETERMINING A POSE OF AT LEAST ONE OBJECT IN AN OPERATING THEATRE

(71) Applicant: CARL ZEISS MEDITEC AG, Jena (DE)

(72) Inventor: Stefan Saur, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 525 days.

(21) Appl. No.: 17/871,081

(22) Filed: Jul. 22, 2022

(65) Prior Publication Data

US 2023/0026585 A1   Jan. 26, 2023

(30) Foreign Application Priority Data

Jul. 23, 2021   (DE) ...................... 10 2021 207 950.4

(51) Int. Cl.
*A61B 34/20*   (2016.01)
*G06T 7/579*   (2017.01)
*G06T 7/70*   (2017.01)

(52) U.S. Cl.
CPC .............. *A61B 34/20* (2016.02); *G06T 7/579* (2017.01); *G06T 7/70* (2017.01); *A61B 2034/2055* (2016.02); *A61B 2034/2065* (2016.02)

(58) Field of Classification Search
None
See application file for complete search history.

(56) References Cited

U.S. PATENT DOCUMENTS

| | | |
|---|---|---|
| 2005/0203380 A1 | 9/2005 | Sauer et al. |
| 2017/0258531 A1 | 9/2017 | Bodjanski |
| 2019/0328464 A1 | 10/2019 | Saur et al. |
| 2021/0090344 A1 | 3/2021 | Geri et al. |
| 2021/0228281 A1* | 7/2021 | Calloway .............. G06T 19/006 |
| 2022/0061921 A1* | 3/2022 | Crawford .................. G06T 7/74 |

FOREIGN PATENT DOCUMENTS

| | | |
|---|---|---|
| DE | 10 2018 206 406 B3 | 9/2019 |
| WO | WO 2006/095027 A1 | 9/2006 |
| WO | WO 2017/157763 A1 | 9/2017 |
| WO | WO 2020/102665 A1 | 5/2020 |

* cited by examiner

*Primary Examiner* — Leon Flores
(74) *Attorney, Agent, or Firm* — NIXON PEABODY LLP; Jeffrey L. Costellia (57) ABSTRACT

The invention relates to a method and a system for determining a pose of at least one object in an operating theatre, in a reference coordinate system of a pose detection device of a surgical microscope, involving the determination of the pose of the object by way of a movably arranged microscope-external pose detection device in a first coordinate system, the first coordinate system being a coordinate system that is arranged to be stationary relative to the operating theatre, the determination of the pose of the reference coordinate system by the non-stationary microscope-external pose detection device in the first coordinate system, and the transformation of the pose of the object from the first coordinate system into the reference coordinate system of the pose detection device of the surgical microscope.

18 Claims, 2 Drawing Sheets

METHOD AND SYSTEM FOR DETERMINING A POSE OF AT LEAST ONE OBJECT IN AN OPERATING THEATRE

CROSS-REFERENCE TO RELATED APPLICATIONS

The present application claims priority under 35 U.S.C. § 119 to German Patent Application No. 10 2021 207 950.4 filed on Jul. 23, 2021, the contents of which are hereby incorporated by reference herein in their entirety.

The invention relates to a method and a system for determining a pose of at least one object in an operating theatre, in a reference coordinate system of a pose detection device of a surgical microscope.

As a rule, multiple objects are arranged in operating theatres that serve the implementation of (neuro)surgical interventions, for example. In addition to an operating table, the operating theatre may contain, e.g., a surgical microscope, a (microscope-external) stereo tracking system, one or more display device(s), one or more device(s) for intraoperative imaging, for example an OCT apparatus, an x-ray apparatus or an ultrasound apparatus.

To make carrying out an intervention easier, and/or to reduce the time required for said intervention, a surgeon may be assisted by a surgical navigation system. The latter facilitates in particular a common representation, in the correct pose, of information produced intraoperatively and information produced preoperatively. By way of example, data obtained intraoperatively may relate to information about the pose of a medical instrument or of intraoperatively produced image data. CT or MRI volume data can be examples of information obtained preoperatively.

So-called tracking systems are used for surgical navigation; these facilitate an intraoperative determination of the pose of objects, especially instruments, in the operating theatre. In particular, stereoscopic systems for capturing the pose of instruments such as pointers or other imaging objects/apparatuses in the operating theatre are known. In order to determine the pose by way of such a system, it is generally necessary to arrange markers or targets with a group of a plurality of markers on the object whose pose is intended to be determined. As a result of the spatial boundary conditions in the operating theatre, there generally is a spatial distance of 1 m or up to 2 m between an imaging unit of the tracking system and the object. However, such a distance also requires a marker or a target to take up a certain spatial volume in order to be able to be imaged by the imaging unit with a resolution that is required for determining the pose. This is disadvantageous, particularly in the case of microsurgical interventions, since for example the instruments are small in this case and the corresponding spatial volume is not available.

Pose detection devices that are integrated into a surgical microscope are also known. These use an image capturing device for microscopic imaging of the surgical microscope or a surround camera separate therefrom, in order, in image-based fashion, to carry out a determination of the pose of objects in the captured region of the corresponding image capturing device. Thus, DE 10 2018 206 406 A1 describes microscopy system having an image capturing device for optical detection of a target. However, a disadvantage in the use of such tracking systems is that these only have a spatially restricted captured region, and consequently no longer detect other objects in the wider surroundings and are therefore unable to determine their pose.

WO 2017/157763 A1 discloses tracking the pose of a spatial position of a medical instrument in a medical work area, with a microscope-integrated camera being used to determine the pose of the instrument in the medical work area. A second video camera is provided for the purposes of determining a relative pose between an anatomical structure and this aforementioned microscope-integrated camera. This consequently allows the surgical microscope to be detected, and allows its pose to be determined, by way of this second camera, with the surgical microscope itself being able to detect the medical instrument by way of the microscope-integrated camera and being able to determine the pose of said medical instrument. A disadvantage in this case is that the detection of the pose of further objects in the surroundings of the surgical microscope requires all these objects to be in the captured region of the second camera at the same time. The latter must therefore be positioned accordingly, and also repositioned during an operation under certain circumstances. As a rule, this requires a lot of time and may interrupt or lengthen an operation. A further disadvantage is that increasing distance also requires appropriate scaling of the size of the marker/the target. Further, tracking systems that operate with a second such camera have a generally unwanted large footprint in the operating theatre.

So-called head-mounted displays (HMD) are also known. US 2021/090344 A1 discloses an HMD having mechanisms for determining a pose and position in relation to a patient, wherein for example a camera is configured in such a way that it detects markers on a patient and, on the basis thereof, detects a position of the surgeon and a line of sight relative to the patient. US 2005/203380 A1 discloses an HMD having at least one tracking camera. WO 2020/102665 A1 discloses what is known as inside-out tracking with one or more cameras fastened to an HMD.

It is however desirable to provide information about a pose in an operating theatre of objects, which are not located in a captured region of the pose detection device of a surgical microscope, in the reference coordinate system of said pose detection device in order to be able to fuse the pose of such objects and/or the information provided by such objects, e.g., intraoperatively produced image data, with the information provided by the pose detection device of the surgical microscope and/or with the (image) information provided by the surgical microscope in a simple manner. In particular, but not exclusively, if intraoperative image data are produced by a surgical microscope, there is the desire to be able to display these quickly, accurately, reliably and, in particular, also in the correct pose in relation to further information, for example also information produced preoperatively.

Hence, a technical problem arising is that of developing a method and a system for determining a pose of at least one object in an operating theatre, which facilitate a quick, accurate, reliable and, in terms of pose, correct determination of information about a pose of objects, in particular in a reference coordinate system of a pose detection device of the surgical microscope.

The solution to the technical problem is provided by the subject matter having the features of the independent claims. Further advantageous configurations of the invention are evident from the dependent claims.

A method is proposed for determining a pose of at least one object in an operating theatre, in a reference coordinate system of a pose detection device of a surgical microscope. The pose detection device of the surgical microscope is also referred to as internal pose detection device below. The reference coordinate system of this pose detection device can be a reference coordinate system of the surgical microscope or can be arranged in stationary fashion relative to this coordinate system.

The method comprises:
- the determination of the pose of the object by way of a movably arranged microscope-external pose detection device in a first coordinate system, the first coordinate system being a coordinate system that is arranged to be stationary relative to the operating theatre,
- the determination of the pose of the reference coordinate system by the non-stationary microscope-external pose detection device in the first coordinate system,
- the transformation of the pose of the object from the first coordinate system into the reference coordinate system of the pose detection device of the surgical microscope.

In this case, an operating theatre can denote a room or room-like region that is set up to carry out operations. In particular, the devices or apparatuses required to carry out an operation are arranged in the operating theatre, inter alia one or more of the objects mentioned at the outset, with the enumeration however not being comprehensive. In particular, an object can be a device for intraoperative imaging, for example a device for producing x-ray images such as for example a C-arm, a device for producing ultrasound images or a device for producing OCT images. An object can also be an instrument, in particular a medical instrument, more particularly a surgical instrument. For example, this includes instruments such as clamps, holders, syringes, tweezers, spatulas, scissors, scalpels, wound hooks, forceps, aspirators, cauterizing tools, but also retractors, e.g. a brain retractor.

The determination of a pose of an object within the meaning of this invention can denote the complete and, in particular, biunique determination of the pose in a target coordinate system, for example the determination of position values of an origin of a Cartesian object coordinate system about three spatial axes of a Cartesian target coordinate system and the determination of three angle values between the three spatial axes of the Cartesian object coordinate system and the three spatial axes of the Cartesian target coordinate system. The target coordinate system can be the reference coordinate system of the corresponding pose detection device. However, the determination of the pose may also denote an incomplete determination of the pose, with for example not all position values and/or not all angle values being determined in this case.

Within the meaning of this invention, a surgical microscope can designate a device for magnified visual presentation of an examination object or examination region. The microscope can be a conventional light microscope, which generates an enlarged image representation by utilizing optical effects, in particular by means for beam guidance and/or beam shaping and/or beam deflection, for example lens elements. However, the microscope can also be a digital microscope, with the image representation to be visualized by the microscope being able to be produced by means of an image capturing device for microscopic imaging and being able to be displayed on an appropriate display device, for example a visual display unit. The surgical microscope may comprise a stand for holding an objective, the latter being able to be mechanically fastened, in particular mechanically movably fastened, for example pivotably fastened, to the free end of the stand. In this case, the stand is designed to facilitate a movement of the objective in space. The surgical microscope can be part of a surgical microscopy system which may comprise further devices, for example a display device, in particular a 3-D display device, in addition to the surgical microscope.

The internal pose detection device the microscope preferably is a monoscopic pose detection device. The latter comprises at least one image capturing device, in particular exactly one image capturing device, for producing two-dimensional image representations of an object, in particular of at least one marker, with a pose, that is to say a three-dimensional position and/or a three-dimensional orientation, of the object being able to be determined by evaluating a two-dimensional image representation, in particular exactly one two-dimensional image representation. In particular, an evaluation of intensity values of pixels (image points) of the two-dimensional image representation can be carried out in order to determine the pose. The internal pose detection device, however, need not necessarily be in the form of a monoscopic pose detection device; it may also be designed differently, for example as a stereoscopic pose detection device.

The image capturing device(s) of the internal pose detection device can be arranged in a housing of the microscope in this case. The image capturing device of the internal pose detection device or of one of these image capturing devices can be the image capturing device for microscopic imaging. However, the image capturing device(s) of the internal pose detection device preferably differ/differs from the image capturing device for microscopic imaging. In this case, a beam path for radiation used for the microscopic imaging can be arranged and/or formed to be different, in particular spatially separated, from the beam path for radiation guided to the image capturing device of the internal pose detection device and used for determining the pose. The beam paths can be formed in a common housing or microscope body of the microscope. Capture regions of these image capturing devices can overlap at least in part.

The microscope-external pose detection device, also referred to as external pose detection device below, may be an optical pose detection device, in particular a monoscopic or stereoscopic pose detection device. Further, it may comprise exactly one or at least two image capturing devices. The image capturing device(s) of the external pose detection device may be RGB cameras. However, it is conceivable for also a different sensor to be used, for example at least one time-of-flight sensor or a gyroscope, or a sensor for determining pose as described in more detail below, and for said different sensor to be part of the microscope-external pose detection device. The external pose detection device, in particular its sensor(s) or image capturing device(s), may be portable in this case and, for example, be integrated in or arranged on a device that is wearable, in particular by a user or surgeon. In particular, the wearable device can be a device that is arrangeable on/fastenable to the head or arm or any other body part. Further, a pose detection device, that is to say the internal and/or the external pose detection device, may comprise at least one lighting device.

The pose can be determined with the assistance of markers. This can mean that exactly one marker or multiple markers is/are arranged on, more particularly fastened to, the object. It is also conceivable that a target is arranged on, more particularly fastened to, the object, with the target comprising exactly one marker or else multiple markers. Multiple markers of an object or of a target can be arranged relative to one another with a predetermined arrangement, that is to say an arrangement known in advance, which facilitates an identification of the object in particular. A marker can in this case be optically detectable and thus also be detectable in the image representation of an image capturing device of a pose detection device, in particular thus have an optically detectable pattern. An optically detectable marker can in particular be what is known as an ARUCO marker or be a marker embodied as described in US 2017/258531 A1. A marker is preferably a passive marker but it may also be an active marker. It is further possible that a marker is a reflective or a non-reflective marker, a phosphorescent or non-phosphorescent marker, and/or a fluorescent or non-fluorescent marker. It is further possible for the pose to be determined without markers. In this case, a geometry of the imaged object, for example, can be evaluated for determining pose. Methods of marker-based and marker-free determination of pose are known to a person skilled in the art.

In this case, the pose information can be determined by means of an evaluation device of the pose detection device. This may be formed as a microcontroller or an integrated circuit or comprise such a microcontroller or integrated circuit. To this end, output signals generated by the image capturing device(s) (image signals) can be transferred to the evaluation device and can be evaluated by the latter for the purposes of determining pose. The fact that the first coordinate system is a coordinate system arranged in stationary fashion relative to the operating theatre can mean that a pose of this coordinate system, that is to say in particular a position of its origin and an alignment of its axes, does not change relative to stationary constituent parts of said operating theatre. By way of example, such stationary constituent parts can be a floor, walls of a room, a ceiling or objects arranged on/fastened to these in stationary fashion. In particular, the first coordinate system can be arranged in stationary fashion in a GNSS coordinate system. The first coordinate system can be a reference coordinate system of the external pose detection device, with the pose being determined in this coordinate system by the external pose detection device. However, there may be a transformation from a coordinate system of a detection device of the external pose detection device into the first coordinate system for the purposes of determining the pose. This transformation or transformation rule may be determined at run time—as will still be explained in more detail below. The pose of the first coordinate system in the operating theatre can be implemented by evaluating signals produced by the external pose detection device, in particular by a device for acquiring surround information of the external pose detection device.

The transformation of the pose of the object from the first coordinate system into the reference coordinate system of the internal pose detection device can be carried out by an evaluation device, in particular by an evaluation device of the surgical microscope. This can be the evaluation device which also carries out the determination of the pose by way of the internal pose detection device. However, it can also be an evaluation device separate therefrom or a microscope-external evaluation device, for example an evaluation device of the external pose detection device or an evaluation device of an overarching system. In particular, the reference coordinate system of the internal pose detection device can be a coordinate system which is arranged in stationary fashion relative to an objective of the surgical microscope, i.e. a coordinate system that is stationary with respect to the objective.

It is possible that the evaluation device then controls a display device, in particular a 3-D display device of the surgical microscope or of a surgical microscopy system comprising the display device and the surgical microscope, in such a way that there is a representation of the object in its correct pose and/or a representation of the information about the object provided intraoperatively (in particular image data) that is in its correct pose with respect to information (in particular image data) produced preoperatively, for example by overlaying, superimposing, and/or using methods for representing virtual or augmented reality. Thus, microscope, x-ray, ultrasound and/or OCT images produced intraoperatively and image data such as CT or MRI data produced preoperatively can, for example, be represented in the correct pose with respect to one another. It is also possible that the evaluation device controls a display device in such a way that there is a representation of the object in its correct position and/or a representation of the information about the object provided intraoperatively (in particular image data) in its correct pose with respect to microscope images that are produced intraoperatively, in particular by way of the method explained above. Thus, x-ray, ultrasound and/or OCT images produced preoperatively and microscope images produced intraoperatively can, for example, be represented in the correct pose with respect to one another.

It is also possible that an object detected by the internal pose detection device is represented in its correct pose in image data produced preoperatively and/or intraoperatively. By determining the pose of the reference coordinate system of the internal pose detection device and the pose of the object in the first coordinate system and by the transformation into the reference coordinate system of the internal pose detection device, it is hence advantageously possible to represent information quickly, accurately, reliably and in the correct pose by way of the surgical microscope or by way of a surgical microscopy system comprising the surgical microscope.

In a further embodiment at least a sensor of the movable microscope-external pose detection device is integrated in, or arranged on, a head-mounted display (HMD). The sensor can denote a detection device that produces output signals which can be evaluated for the purposes of determining pose, in particular by way of an evaluation device. It is possible for the evaluation device likewise to be integrated in, or arranged on, the HMD. However, it is also possible for the evaluation device not to be integrated in, or arranged on, the HMD.

The HMD can serve to represent an object in a virtual and/or augmented reality for the wearer. The HMD can have a glasses-type design, in particular as a pair of VR and/or AR glasses. In particular, the HMD can be designed in such a way that a wearer is able to perceive the real objects in the operating theatre located in their field of view, with, in addition to these real objects, virtual objects being able to be overlaid into the field of view, for example in the form of an overlay, in particular a transparent overlay, or a replacement of real objects. By way of example, it is possible that the wearer is able to visually capture the information represented on a display device in the operating theatre, in particular microscopic image representations provided by the surgical microscope, with at least one additional item of information, in particular at least one virtual object, for example information produced preoperatively and/or intraoperatively, being able to be displayed for the wearer by way of the HMD, in particular in the correct pose. In addition to the superimposition of such information/objects, the HMD also comprises a pose detection device or at least a part thereof, in particular a sensor-type part. This allows partial or complete determination of the pose of an object in the capture region, in particular in a reference coordinate system of the HMD. In this case, the capture region of the pose detection device can comprise or at least partly overlap with the field of view of a wearer provided by the HMD. A head movement of the wearer also changes a pose of the capture region. Head movements, for example for scanning the operating theatre, thus facilitate the provision of a large spatial capture region of the external pose detection device in a simple manner, in particular by virtue of the capture regions in the various poses being fused to form a resultant capture region. Thus, there is advantageously a simple provision of the external pose detection device with a large capture region by way of integrating the pose detection device into the HMD.

In a further embodiment, the pose of the microscope-external pose detection device or at least the pose of the sensor of said microscope-external pose detection device remains constant between the determination of the pose of the object by the microscope-external pose detection device and the determination of the pose of the reference coordinate system. Expressed differently, the pose of the object and the surgical microscope is determined by the external pose detection device when both are located in the (pose-specific) capture region of the external pose detection device in a current pose thereof. Advantageously, this facilitates a reliable and accurate determination of the poses in a common coordinate system, specifically the first coordinate system, since possible changes in pose of the external pose detection device between the determination of the pose have to be taken into account.

Alternatively, the pose is altered between the determination of the pose of the object by the microscope-external pose detection device and the determination of the pose of the reference coordinate system Expressed differently, the pose of the object and of the surgical microscope is determined by the external pose detection device in different poses of the external pose detection device, with for example the object but not the surgical microscope being situated in the capture region of the external pose detection device in a first pose and the surgical microscope but not the object being situated in said capture region in an altered pose. This advantageously facilitates a reliable determination of the poses in a common coordinate system even if the surgical microscope and the object are not located together in the capture region of the external pose detection device in a current pose of the latter, for example if they are arranged at great distance from one another in the operating theatre. It is possible for the pose to be altered in such a way that the capture region of the external pose detection device before the change in pose has a common region with the pose of the capture region after the change in pose, or for the capture regions in the two poses to be disjoint.

In a further embodiment the microscope-external pose detection device comprises at least an image capturing device and/or at least a time-of-flight sensor and/or at least a depth sensor and/or a device for detecting surfaces for determining pose. In particular, these may form the aforementioned sensor of the external pose detection device. Expressed differently, at least one sensor for determining pose can be integrated into the external pose detection device, with the determination of the pose being able to be performed by evaluating the output signals of the sensor. There can be a monoscopic determination of the pose in the case of an image capturing device, in particular an RGB camera or an infrared camera.

Additionally, the sensor can be an ultrasound sensor, a radar sensor or a lidar sensor. Determining the pose using at least one image capturing device is advantageous, in particular in the case of a marker-assisted determination of the pose, since a high lateral resolution (in the image plane) and hence a great accuracy are regularly provided and/or it is possible to determine a texture and/or colour information, in particular RGB information, which facilitate a reliable identification of the marker. This is particularly advantageous when the pose is determined on the basis of the optical detection of a plurality of different markers. The use of a time-of-flight sensor and/or at least one depth sensor and/or a device for detecting surfaces is advantageous when determining the pose without markers in particular since this allows depth information to be determined, which in turn facilitates the fast, accurate and reliable determination of information about a 3-D geometry, for example about a shape of an instrument, with the latter then being able to be evaluated for determining the pose.

Preferably, the microscope-external pose detection device comprises a plurality of devices or sensors for determining pose, in particular at least one image capturing device and at least one sensor for capturing depth information, for example a time-of-flight a sensor, a depth sensor or a device for capturing surfaces. The pose of an object can be determined by methods of sensor fusion, with the pose information produced by the plurality of sensors being combined in such a method in order to determine the pose. In particular, output signals of the plurality of sensors can be combined/fused, with the pose then being determined on the basis of these fused output signals. It is also possible to combine/fuse sensor-specific pose information determined by evaluating the output signals of the respective sensor, with the pose then being determined on the basis of these fused items of pose information.

Further, it is possible that the external pose detection device comprises an illumination device. By way of example, the latter can serve to produce structural illumination, with image data produced by an image capturing device under the structural illumination being able to be evaluated for the purposes of determining the pose. The illumination device can also be an IR illumination device.

In a further embodiment the pose of the first coordinate system is determined or defined by evaluating output signals of at least one device for acquiring surround information of the microscope-external pose detection device, the device or at least a part thereof being integrated in, or arranged on, the microscope-external pose detection device. Expressed differently, the external pose detection device may comprise the at least one device for acquiring surround information. The latter serves to acquire information about a surround of the external pose detection device. By way of example, it may produce output signals that are dependent on the pose and/or shape of an object in its capture region. The evaluation of the output signals then facilitates for example the determination of the pose of the object in a coordinate system of the device or in the coordinate system of the external pose detection device should a transformation from the coordinate system into the coordinate system of the external pose detection device be known, for example as a result of a calibration. The device for acquiring surround information can be designed as a surround sensor or as a surroundings sensor or may comprise one or more surround sensors.

The evaluation of output signals of the device in particular facilitates the determination or creation of a space model, with a coordinate system of the space model being able to be the first coordinate system. By way of example, the space model may provide information about objects in the capture region of the at least one device for acquiring surround information, in particular about the pose thereof, preferably in the first coordinate system, and/or in relation to the shape thereof. In particular, the space model can be a 3-D model of the operating theatre, created on the basis of the output signals of the device for acquiring surround information. It is conceivable that information known in advance is also used in addition to the output signals to create the space model, for example a pose, known in advance, of objects arranged on the operating theatre, in particular of objects arranged in stationary fashion relative to the operating theatre. By way of example, such information can be construction data such as floorplan data. By way of example, this information may be provided by a database.

In particular, the space model can allow the pose of the external pose detection device to be determined in the first coordinate system by evaluating output signals of the at least one device for acquiring surround information. Consequently, it is possible to determine a transformation rule from a coordinate system of the external pose detection device to the first coordinate system. However, in that case it is also possible to determine, in the first coordinate system, the pose of the object determined by the external pose detection device. In particular, for this purpose, a pose of the object can be determined in the coordinate system of the external pose detection device and can then be transformed into the first coordinate system by means of the aforementioned transformation rule.

The device for acquiring surround information may comprise one, multiple or else, preferably, all sensor(s) for determining pose, that is to say one or more sensor(s) whose output signals are also used for determining pose by the external pose detection device. However, it is also possible to use a sensor whose output signals are not used by the external pose detection device for determining pose, that is to say a sensor different therefrom. Preferably, the device comprises at least one image capturing device and at least one device for producing depth information. Additionally, the device for acquiring surround information may comprise a device for determining the pose of the microscope-external pose detection device, for example be formed as, or comprise, a gyroscope. This device for determining the pose of the microscope-external pose detection device can for example determine the relative spatial position of the portable device, in which the microscope-external pose detection device or at least one sensor of said pose detection device is integrated.

What determining or defining the pose of the first coordinate system on the basis of output signals of a device for acquiring surround information advantageously facilitates is that the determination of the pose of the surgical microscope and of the object by means of the external pose detection device can be implemented quickly, in particular without renewed calibration or registration processes, even if the pose of the external pose detection device changes, in particular at runtime of the method. A further advantage of such a definition is that the surgical microscope and the object need not be located in the capture region of the microscope-external pose detection device at the same time.

In a further embodiment the pose of the first coordinate system and/or a pose of the microscope-external pose detection device is updated in the first coordinate system at run time. In particular, the above-described space model can be updated at run time, for example continuously and after a predetermined time interval has expired. This advantageously increases the reliability of the pose determination, in particular if a pose of the reference coordinate system of the internal pose detection device and/or of an object has changed in the first coordinate system.

In a further embodiment a SLAM method is carried out to determine/define the pose of the first coordinate system. Such SLAM methods (simultaneous localization and mapping methods) are known to a person skilled in the art. Hence, there can advantageously be a simple, accurate and reliable determination of the pose of the first coordinate system, and hence also of the object in the reference coordinate system of the internal pose detection device.

In a further embodiment information about the pose of the reference coordinate system in the first coordinate system and about the pose of the object in the first coordinate system is transferred to an evaluation device of the surgical microscope, the evaluation device carrying out the transformation of the pose of the object into the reference coordinate system of the internal pose detection device. The evaluation device may be formed as a microcontroller or an integrated circuit or comprise such a microcontroller or integrated circuit. The evaluation device may additionally be the evaluation device for determining the pose of the internal pose detection device. Additionally, the evaluation device may be part of a control device of the surgical microscope which for example controls an operation of the surgical microscope, for example a movement of the surgical microscope, an adjustment of the magnification and/or of the focus, and/or an illumination by illumination devices of the microscope. Additionally, the control device can produce control data or control signals for controlling a display device in order to bring about the aforementioned representation of information in the correct pose on the display device. As a result of the transfer to the evaluation device of the surgical microscope there advantageously is a quick use of the pose information by the surgical microscope, in particular without unwanted latencies, in particular for fusing the pose information with the information produced by the surgical microscope.

In a further embodiment, information about the pose of at least one further object in the operating theatre is determined by the pose detection device of the surgical microscope. In particular, the further object can be the object whose pose is determined or rendered determinable by the external pose detection device. However, the further object preferably is an object whose pose is not determined or is not rendered determinable by the external pose detection device. In particular, the further object can be an object arranged in the capture region of the internal pose detection device, for example a medical instrument. Then it is possible to determine the pose of the reference coordinate system of the internal pose detection device, the pose of the object and the pose of the further object in the reference coordinate system, in particular by way of the evaluation device of the surgical microscope. By way of example, as a result of this, it is possible that the further object can be displayed in the correct pose with the object detected by the external pose detection device or the information produced by this object intraoperatively and/or with the information produced intraoperatively by the surgical microscope and/or with information produced preoperatively.

A system is also proposed for determining a pose of at least one object in an operating theatre, in a reference coordinate system of a pose detection device of the surgical microscope. In particular, the system is configured to carry out a method according to one of the embodiments described in this embodiment. Expressed differently, such a method can be carried out by the system.

The system comprises at least the pose detection device of the surgical microscope and a movably arranged microscope-external pose detection device, and an evaluation device. The system is configured to carry out the following steps:

the determination of the pose of the object by way of a movably arranged microscope-external pose detection device in a first coordinate system, which is a reference coordinate system of the microscope-external pose detection device, the determination of the pose of the reference coordinate system by the non-stationary microscope-external pose detection device in the first coordinate system, the transformation of the pose of the object from the first coordinate system into the reference coordinate system of the pose detection device of the surgical microscope.

The internal pose detection device may comprise at least one or exactly one image capturing device for microscopic imaging and/or at least one or exactly one image capturing device for determining pose, which differs from the image capturing device for microscopic imaging. Further, the system may comprise data or signal transfer means for transferring data/signals between the evaluation device, the internal pose detection device and/or the external pose detection device. These can be designed for wireless or wired data transfer. Further, the system may comprise one or more constituent parts of the above-described internal and/or external pose detection device. The proposed system advantageously facilitates the implementation of one of the embodiments of the method described in this disclosure, with the corresponding technical advantages. The system can be integrated into an operating theatre.

In a further embodiment the movable microscope-external pose detection device is integrated in, or arranged on, a head-mounted display. This and corresponding technical advantages have already been explained above.

In a further embodiment at least an image capturing device and/or at least a time-of-flight sensor and/or at least a depth sensor and/or a device for detecting surfaces for determining pose is integrated in, or arranged on, the head-mounted display. This and corresponding technical advantages have already been explained above.

In a further embodiment at least a device for acquiring surround information is integrated in, or arranged on, the head-mounted display. This and corresponding technical advantages have already been explained above. In particular, this device may comprise one, multiple or all devices for determining pose, which are integrated in, or arranged on, the HMD. Thus, in this case a device for determining pose corresponds to the device for acquiring surround information or a constituent part of this device.

In a further embodiment the system comprises at least one display device, which is controllable by the evaluation device for representing, in the correct pose, the object in data produced preoperatively and/or intraoperatively. This and corresponding technical advantages have already been explained above.

The invention will be illustrated in more detail on the basis of exemplary embodiments. In the figures.

Identical reference signs hereinafter denote elements having identical or similar technical features.

Figure 1:
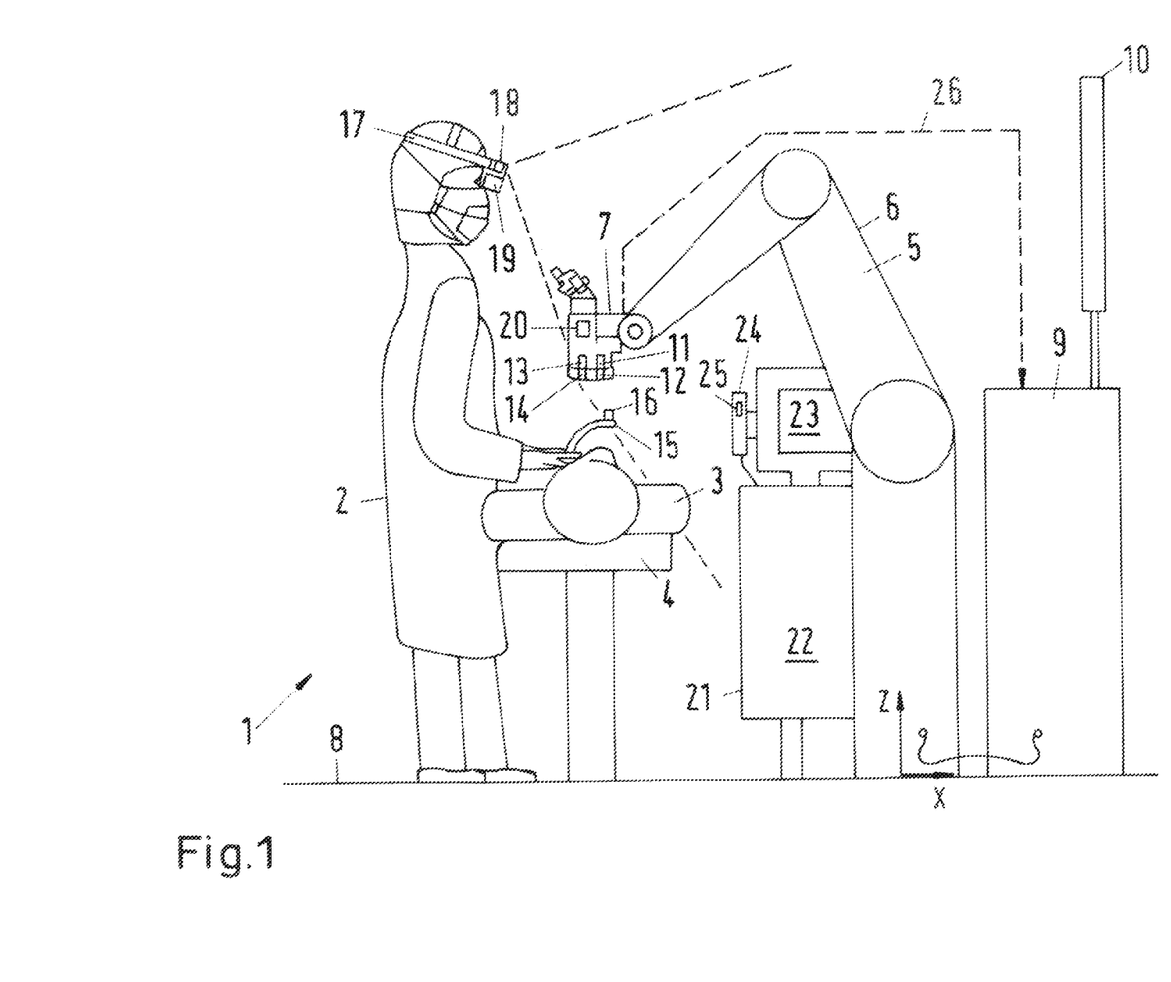
FIG. 1 shows a schematic illustration of an operating theatre.

FIG. 1 shows a schematic representation of an operating theatre 1. A surgeon 2 and a patient 3 lying on an operating table 4 in the operating theatre 1 are depicted. A surgical microscope 5 with a stand 6 and an objective 7 is also depicted. The objective 7 is arranged on a free end of the stand 6. Drive devices of the surgical microscope 5, not depicted here, facilitate a change in a position and orientation of the objective 7, in particular in a first coordinate system which is a Cartesian coordinate system and which comprises a longitudinal axis X and a vertical axis Z. The first coordinate system is arranged in stationary fashion with respect to the operating theatre 1, in particular relative to a floor 8 of the operating theatre 1. A transverse axis, which may be oriented perpendicular to the depicted longitudinal and vertical axes X, Z, is not depicted. The vertical axis Z can be oriented in parallel and opposed to the force of gravity, in particular.

A control and evaluation device 9 of the surgical microscope 5 and a display device 10, in particular a 3-D display device, which may be part of a surgical microscopy system comprising the surgical microscope 5, are also depicted. It is possible, in particular, that the control and evaluation device 9 controls a display device 10 to display information, in particular by way of interfaces suitable to this end.

The surgical microscope 5, in particular the objective 7, is further depicted as comprising a surround camera 11, which may be arranged in a housing of the objective 7. A beam path 12, along which beams for capture by the surround camera 11 extend, is likewise depicted schematically. An image capturing device 13 of the surgical microscope 5 for microscopic imaging and a beam path 14 along which beams for capture by way of this image capturing device 13 extend are also depicted schematically. The image capturing device 13 and the beam paths 12, 14 are also arranged in the housing of the objective 7, with the beam paths being formed separately.

In this case, the surround camera 11 is part of a pose detection device of the surgical microscope 5, that is to say part of an internal pose detection device. A data connection 26 is depicted schematically, it can be used to transfer the image data of the surround camera 11 to the control and evaluation device 9, with the latter then determining pose. The reference coordinate system of the internal pose detection device may be a coordinate system that is stationary with respect to the objective. Consequently, a pose determined by the internal pose detection device can be determined in this reference coordinate system.

Hence, the pose of an instrument 15 held by the surgeon 2, for example, can be determined in the reference coordinate system of the internal pose detection device. In particular, the pose can be determined by evaluating precisely one image representation produced by the two-dimensional surround camera 11. For the purposes of determining pose, the instrument 15 may comprise a marker 16, which is imaged by the surround camera 11, with the corresponding image information being able to be evaluated by the control and evaluation device 9 for determining pose.

A head-mounted display 17 worn by the surgeon 2 on the head is also depicted. The HMD 17 comprises an image capturing device 18 and a display means/device for detecting information from a virtual and/or augmented reality. The image capturing device 18 can be part of a microscope-external pose detection device (external pose detection device).

What is not depicted is that the HMD 17 comprises an evaluation device which facilitates the pose of an object in a coordinate system stationary with respect to the HMD.

This coordinate system stationary with respect to the HMD can be a reference coordinate system of the external pose detection device. Further, this evaluation device can transform the pose information determined in this way, from the coordinate system stationary with respect to the HMD, for example a coordinate system of the image capturing device 18, to the first coordinate system, as a result of which the pose of an object can be determined in the first coordinate system by the external pose detection device. The evaluation device may be integrated into the HMD 17 but may also be formed by the control and evaluation device 9. Alternatively or cumulatively with the image capturing device 28, the external pose detection device may also comprise a time-of-flight sensor and/or a depth sensor and/or a device for capturing surfaces for determining pose.

Further, the HMD may comprise at least one device, not depicted, for acquiring surround information, the output signals of which can be evaluated for the purposes of determining a pose of the first coordinate system or for defining the pose of the first coordinate system relative to the operating theatre, in particular in a global coordinate system, for example a coordinate system stationary with respect to the ground, for example a geocentric coordinate system.

Further, information about the pose of the object in the first coordinate system or output signals of the image capturing device 18 can be transferred to the control and evaluation device 9 by way of means for data transfer, not depicted here.

What is further depicted is that the objective 7 has a marker 20 which is fastened to a housing of the objective 7. This marker 20 can be imaged by the image capturing device 18 of the HMD 17 and can serve to determine the pose of the objective 7. As described above in relation to an object, it is consequently possible to determine a pose of the objective 7 of the surgical microscope 5 in the first coordinate system by way of the external pose detection device. This in turn allows the determination of a pose of the reference coordinate system of the internal pose detection device in the first coordinate system by way of the external pose detection device.

An intraoperative ultrasound apparatus 21, comprising a base 22, a display device 23 and an ultrasonic head 24, to which a marker 25 has likewise been fastened, is also depicted. It is possible that the surgeon 2 or further surgeon or assistant (not depicted here) actuates the ultrasonic head 24 for intraoperative imaging and to this end moves the latter relative to the patient 3, in particular in a state touching/in contact with the patient 3. In this case, the external pose detection device can also determine a pose of the ultrasonic head 24 in the first coordinate system by evaluating precisely one image representation or multiple image representations produced by the image capturing device 18 of the HMD 17.

This pose information can also be transferred to the control and evaluation device 9. Consequently, this advantageously allows the image data produced intraoperatively by the intraoperative ultrasound apparatus 21 and the image data produced by the objective 7, in particular the image data of the image capturing device 13 for microscopic imaging, which can be determined in a reference coordinate system of the internal pose detection device, in particular in the coordinate system that is stationary with respect to the objective, to be represented in the correct pose in relation to one another on the display device 10. Further, it is possible that the pose of the instrument 15, which is determined by the internal pose detection device, is likewise represented in the correct pose in relation to the image information produced by the ultrasonic apparatus 21 and/or in the correct pose in relation to the image information produced by the image capturing device 13 of the surgical microscope 5. Naturally, it is alternatively or cumulatively also possible for data produced preoperatively, in particular image data, to be represented in the correct pose on the display device 10.

Figure 2:
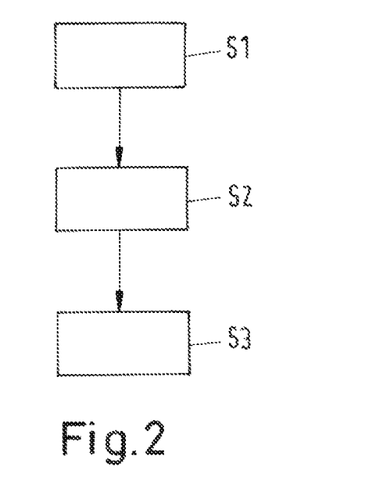
FIG. 2 shows a schematic flowchart of a method according to the invention.

FIG. 2 shows a schematic flowchart of a method according to the invention. In a first step S1, there is a determination of the pose of an object by way of a movably arranged external pose detection device in a first coordinate system (see FIG. 1), the first coordinate system being a coordinate system that is arranged to be stationary relative to the operating theatre 1. In particular, the object can be an intraoperatively imaging object, for example the imaging ultrasound apparatus 21 depicted in FIG. 1. The external pose detection device or a part thereof can be integrated in an HMD 17 (see FIG. 1) in particular.

In a second step S2, there is a determination of the pose of a reference coordinate system of a pose detection device of a surgical microscope 5 in the first coordinate system. As explained above, this reference coordinate system can in particular be a coordinate system stationary with respect to the objective. In a third step S3, there then is a transformation of the pose of the object from the first coordinate system to the reference coordinate system of the internal pose detection device.

In particular, it is possible to determine a transformation rule for transforming a pose in a coordinate system stationary with respect to the object to the first coordinate system. As a result of this, it is possible for example to transform pose information of image information produced by the object and consequently also produced relative to a coordinate system stationary with respect to the object into the first coordinate system.

The determination of the pose of the reference coordinate system of the internal pose detection device in the first coordinate system facilitates the determination of a transformation from the first coordinate system to this reference coordinate system. Consequently, it is possible that the pose information of the image information explained above can be transformed into the reference coordinate system of the internal pose detection device.

It is possible that the pose of the external pose detection device, in particular in the first coordinate system, changes or else remains constant between the first step S1 and the second step S2.

Figure 3:
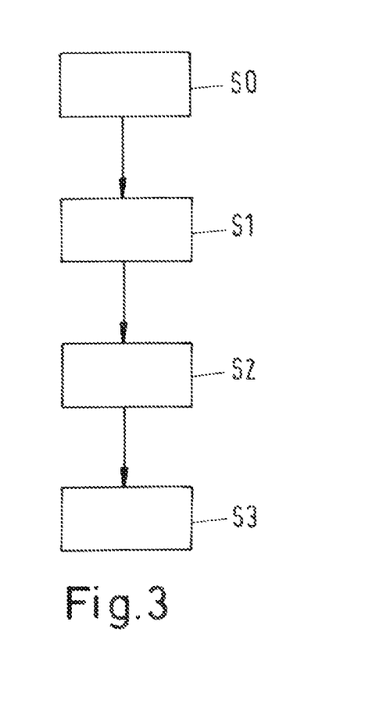
FIG. 3 shows a schematic flowchart of a method according to the invention.

FIG. 3 shows a schematic flowchart of a method according to the invention in a further embodiment. In contrast to the embodiment represented in FIG. 2, the method comprises a pose determination step S0, in which the pose of the first coordinate system is defined by the external pose detection device itself, in particular by evaluating output signals of at least one device for acquiring surround information of the external pose detection device. By way of example, what is known as a SLAM method can be carried out to this end.

In relation to the exemplary embodiment depicted in FIG. 1, the surgeon 2 for example can carry out a movement with their head that scans the operating theatre 1, as a result of which the capture region of the device for acquiring surround information of the HMD 17 is moved through the operating theatre 1. On the basis of the output signals of the surround sensor produced thereby it is then possible to carry out a SLAM method. In particular, it is possible to produce a space model, with the first coordinate system being assigned as a reference coordinate system to the space model. It is possible that the image capturing device 18, which also serves to determine pose by the external pose detection device, forms the device for acquiring surround information for defining the pose of the first coordinate system. Naturally, it is also conceivable that such a device is formed differently from the image capturing device 18.

It is further possible that the pose of the first coordinate system and/or the pose of the external pose detection device in the first coordinate system is updated at run time, for example by way of a continuation of the SLAM method. It is not mandatory for the pose determination step S0 to be carried out before the sequence of first, second and third step S1, S2, S3. Thus, the determination/definition of the pose of the first coordinate system and/or the pose of the external pose detection device in the first coordinate system can also be carried out parallel in time with the sequence of steps S1, S2, S3. In particular, the first step S1 or the information produced in the process, for example image representations of objects in the operating theatre 1, can be used to determine the pose of the first coordinate system and/or the pose of the external pose detection device in the first coordinate system.

LIST OF REFERENCE SIGNS

1 Operating theatre
2 Surgeon
3 Patient
4 Operating table
5 Surgical microscope
6 Stand
7 Objective
8 Floor
9 Control and evaluation device
10 Display device
11 Surround camera
12 Beam path
13 Image capturing device for microscopic imaging
14 Beam path
15 Instrument
16 Marker
17 HMD
18 Image capturing device
19 Display means
20 Marker
21 Ultrasound apparatus
22 Stand
23 Display device
24 Ultrasonic head
25 Marker
26 Data connection
S1 First step
S2 Second step
S3 Third step
S0 Pose determination step
X Longitudinal axis
Z Vertical axis Identical reference signs hereinafter denote elements having identical or similar technical features.

The invention claimed is:

1. A method for determining a pose of at least one object in an operating theatre, in a reference coordinate system of a pose detection device of a surgical microscope, the method comprising: determining the pose of the object by way of a movably arranged microscope-external pose detection device in a first coordinate system, the first coordinate system being a coordinate system that is arranged to be stationary relative to the operating theatre, determining the pose of the reference coordinate system by a non-stationary microscope-external pose detection device in the first coordinate system, transforming the pose of the object from the first coordinate system into the reference coordinate system of the pose detection device of the surgical microscope, wherein the transformed pose is usable to generate a representation of the at least one object.

2. The method according to claim 1, wherein at least a sensor of the movable microscope-external pose detection device is integrated in, or arranged on, a head-mounted display.

3. The method according to claim 1, wherein the pose of the microscope-external pose detection device remains constant or is altered between the determination of the pose of the object by the microscope-external pose detection device and the determination of the pose of the reference coordinate system.

4. The method according to claim 1, wherein the microscope-external pose detection device comprises at least an image capturing device and/or at least a time-of-flight sensor and/or at least a depth sensor and/or a device for detecting surfaces for determining pose.

5. The method according to claim 1, wherein the pose of the first coordinate system is determined/defined by evaluating output signals of at least one device for acquiring surround information of the microscope-external pose detection device, the device for acquiring surround information being integrated in, or arranged on, the microscope-external pose detection device.

6. The method according to claim 5, wherein the pose of the first coordinate system and/or a pose of the microscope-external pose detection device is updated in the first coordinate system at run time.

7. The method according to claim 5, wherein a SLAM method is carried out to determine/define the pose of the first coordinate system.

8. The method according to claim 1, wherein information about the pose of the reference coordinate system in the first coordinate system and about the pose of the object in the first coordinate system is transferred to an evaluation device of the surgical microscope, the evaluation device carrying out the transformation of the pose of the object into the reference coordinate system of the pose detection device of the surgical microscope.

9. The method according to claim 1, wherein information about the pose of at least one further object in the operating theatre is determined by the pose detection device of the surgical microscope.

10. A system for determining a pose of at least one object in an operating theatre, in a reference coordinate system of a pose detection device of a surgical microscope, with the system at least comprising the pose detection device of the surgical microscope and a movably arranged microscope-external pose detection device and an evaluation device, the system being configured to carry out the following steps: determining the pose of the object by way of the movably arranged microscope-external pose detection device in a first coordinate system, the first coordinate system being a coordinate system that is arranged to be stationary relative to the operating theatre, determining the pose of the reference coordinate system by a non-stationary microscope-external pose detection device in the first coordinate system, transforming the pose of the object from the first coordinate system into the reference coordinate system of the pose detection device of the surgical microscope, wherein the transformed pose is usable to generate a representation of the at least one object.

11. The system according to claim 10, wherein at least a sensor of the movable microscope-external pose detection device is integrated in, or arranged on, a head-mounted display.

12. The system according to claim 10, wherein the pose of the microscope-external pose detection device remains constant or is altered between the determination of the pose of the object by the microscope-external pose detection device and the determination of the pose of the reference coordinate system.

13. The system according to claim 10, wherein the microscope-external pose detection device comprises at least an image capturing device and/or at least a time-of-flight sensor and/or at least a depth sensor and/or a device for detecting surfaces for determining pose.

14. The system according to claim 10, wherein the pose of the first coordinate system is determined/defined by evaluating output signals of at least one device for acquiring surround information of the microscope-external pose detection device, the device for acquiring surround information being integrated in, or arranged on, the microscope-external pose detection device.

15. The system according to claim 14, wherein the pose of the first coordinate system and/or a pose of the microscope-external pose detection device is updated in the first coordinate system at run time.

16. The system according to claim 14, wherein a SLAM method is carried out to determine/define the pose of the first coordinate system.

17. The system according to claim 10, wherein information about the pose of the reference coordinate system in the first coordinate system and about the pose of the object in the first coordinate system is transferred to an evaluation device of the surgical microscope, the evaluation device carrying out the transformation of the pose of the object into the reference coordinate system of the pose detection device of the surgical microscope.

18. The method according to claim 10, wherein information about the pose of at least one further object in the operating theatre is determined by the pose detection device of the surgical microscope.

* * * * *